United States Patent [19]

Nakajima

[11] 4,408,602
[45] Oct. 11, 1983

[54] LASER KNIFE DEVICE

[75] Inventor: Tohru Nakajima, Tokyo, Japan

[73] Assignee: Asahi Kogaku Kogyo Kabushiki Kaisha, Tokyo, Japan

[21] Appl. No.: 224,997

[22] Filed: Jan. 14, 1981

[51] Int. Cl.³ .............................................. A61B 17/36
[52] U.S. Cl. ................. 128/303.1; 128/395; 219/121 LS
[58] Field of Search ...................... 128/303.1, 395–398; 219/121 LS

[56] References Cited

U.S. PATENT DOCUMENTS

| | | | |
|---|---|---|---|
| 3,710,798 | 1/1973 | Bredemeier | 128/303.1 |
| 3,796,220 | 3/1974 | Bredemeier | 128/303.1 |
| 3,865,114 | 2/1975 | Sharon | 128/303.1 |
| 4,289,378 | 9/1981 | Remy | 128/303.1 X |

FOREIGN PATENT DOCUMENTS 2809007  9/1979  Fed. Rep. of Germany ... 128/303.1

Primary Examiner—Lee S. Cohen
Attorney, Agent, or Firm—Sughrue, Mion, Zinn, Macpeak and Seas

[57] ABSTRACT

A laser knife with which a laser beam having at least two different wavelengths to thereby eliminate undesirable effects on body tissue, blood and body fluids. First and second laser sources provide first and second operating light beams of different wavelengths. The first and second operating light beams are focused along the same optical axis with the focus points being independently controllable. An illuminating or guide light beam is also provided along the same optical axis which also can be independently focused.

5 Claims, 1 Drawing Figure

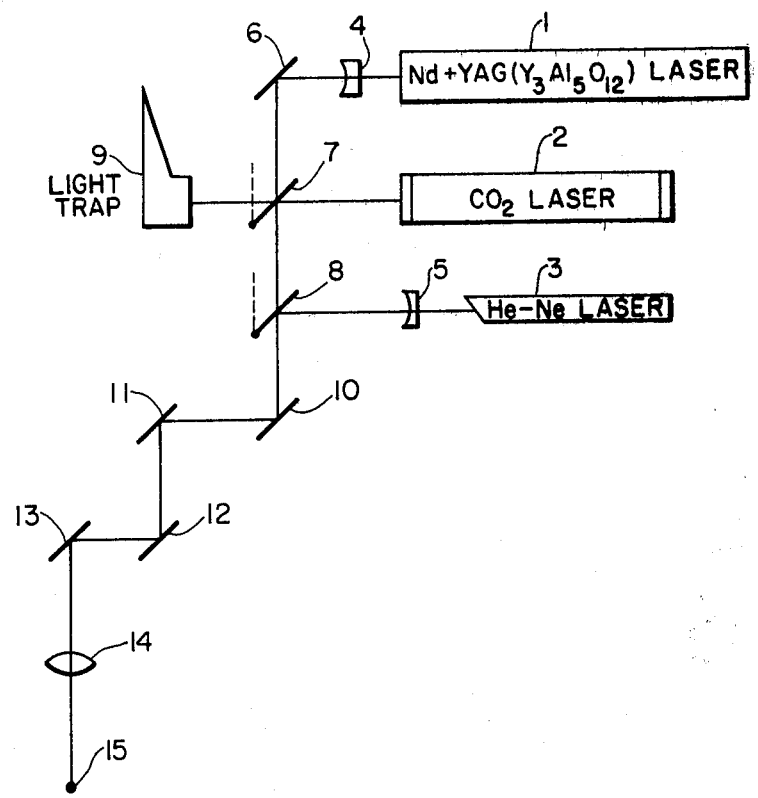

LASER KNIFE DEVICE

BACKGROUND OF THE INVENTION

The present invention relates to a medical laser knife device.

In a laser knife device, a laser beam of 10.6 micron wavelength emitted by a $CO_2$ laser is used to effectively break, remove or cut body tissue. The reason for the use of such a laser beam is that body tissue is made up of 75 to 90% water, water absorbs effectively infrared rays having a wavelength greater than 2.5 microns, and a $CO_2$ laser beam has an extremely high energy conversion efficiency.

In a laser knife device of this general type, the laser beam emitted from the laser device is introduced through a multiarticulation type flexible light conducting device called "a manipulator" to a focusing lens provided at the end of the manipulator. The laser beam is focused by the focusing lens to obtain a very high energy density and the laser beam thus focused is applied to a desired part of the body to generate a high temperature of 1,500° to 1,600° C. momentarily to cut designated body tissue. Upon application of the laser beam, capillary vessels smaller than about 0.7 mm in diameter are automatically sealed and accordingly an operation can be achieved with little or no bleeding. On the other hand, if the part to be operated on is intricate anatomically, it is often required to cut or coagulate a part of tissue which is covered by lymph without evaporating the lymph. A specific example of this will be described.

The cochlear duct forming a part of the inner ear of a human being is located inside the temporal bone. In the cochlear duct, a membranous labyrinth is formed along the modiolus where the auditory sense cells are located. If the auditory sense cells become abnormal, whole or partial deafness or continuous tinnitus can result. In order to cure tinnitus, an operation of breaking or coagulating a part of the auditory sense cells on the membranous labyrinth has been performed by using a focused ultrasonic beam. However, in many cases it has been difficult to completely cure the tinnitus.

The use of a laser knife for such an operation is effective. In this case, an operating technique is employed in which a thin laser beam (hereinafter referred to as "an operating light beam" when applicable) is applied from near the bone window of the inner ear, namely, the round window which is located behind and below the tympanic cavity. First, a minute hole is cut in the bone window to allow the operating light beam to enter the cochlear duct through the minute hole as a result of which the operating light beam is applied through the lymph layer in the outer lymph space around the auditory sense cells. However, since lymph is substantially made up of water, the lymph is instantly evaporated by the operating light beam as a result of which the pressure is in the cochlear duct is abruptly increased which can, at worst, break the entire cochlear duct.

Accordingly, an object of the invention is to provide a laser knife device in which the above-described difficulties accompanying a conventional laser knife device have been effectively eliminated.

SUMMARY OF THE INVENTION

In accordance with this and other objects of the invention, there is provided a laser knife device including means for providing first and second operating light beams and means for focusing the first and second operating light beams on the same optical axis. A guide light beam is coincided with the focus of the first operating light beam on the optical axis. Control means is provided for positioning the focus of the second operating light beam at a position within a predetermined range around the focus of the first operating light beam, that is, either in front of, at, or behind the focus of the first operating light beam. The control means is preferably a focus position correcting lens disposed in the path of the second operating light beam only. Movable mirrors may be provided for controlling the guide or illuminating light beam and the first operating light beam so that these can be directed along the optical axis or not as desired.

BRIEF DESCRIPTION OF THE DRAWINGS

The single FIGURE in the accompanying drawing is an explanatory diagram showing the arrangement of a laser knife device according to the invention.

DESCRIPTION OF THE PREFERRED EMBODIMENTS

The invention will be explained with reference to a preferred embodiment shown in the accompanying drawing.

In the single FIGURE in the accompanying drawing, reference numeral 1 designates, for instance, an $Nd+YAG(Y_3Al_5O_{12})$ laser device for emitting a second operating light beam; 2 a $CO_2$ laser device for emitting a first operating light beam; 3 a He-Ne laser device for emitting a guide light beam; 4 and 5 focus position correcting lenses; and 6, 10, 11, 12 and 13 surface reflection mirrors. The mirrors 6, 10, 11, 12 and 13 are 45° reflection mirrors which are located in corresponding mirror mounts. The mirror mounts are rotatably coupled to one another through cylindrical members thus forming a multi-articulation type flexible light conducting path or manipulator.

Further in the single FIGURE, reference numerals 7 and 8 designate movable mirrors which are retractable from the optical path, 9 a trap, and 14 a focusing lens which focuses rays at a point 15. The manipulator is made up of the mirror mounts and the cylindrical members which extend nearly to the focal point of the focusing lens 15 for providing the flexible light conducting path and for security.

In a surgical operation, the operator grips the end portion of the manipulator with his hand and moves it to the desired part of the body and irradiates the desired part with the operating light beam. The guide light beam is adapted to indicate the focal point of the operating light beam as a visible light spot before the operating light beam is applied. That is, the operating light beam is applied to the same position as the guide light beam spot. Therefore, the operator can start the operating light beam emitting laser device, such as by operating a foot pedal after the guide light beam spot is shone on the desired location. For this purpose, the movable mirror 8 is so designed that it is retracted from the optical path simultaneously when the foot pedal is operated. A mechanism for retracting the movable mirror 8 is not shown as a variety of appropriate mechanisms are well-known in the art. The position of the mirror in the retracted position is indicated by a dotted line in the FIGURE.

The refractive index of the focusing lens (made of ZnSe for instance) for the guide beam (having a wavelength of $0.6328\mu$) is different from that of the focusing lens for the first operating light beam (having a wavelength of $10.6\mu$). Therefore, the focus position correcting lens 5 is disposed on the optical axis to cause the focus position of the guide light beam to coincide with that of the first operating light beam.

After applying the guide light beam to the desired part of the body, the operator operates the foot pedal, to emit the first operating light beam. It is preferable that the foot pedal be so designed that it can be operated in two steps so that the second operating light beam can be emitted in succession with the emission of the first operating light beam. In this case, when the foot pedal is depressed past the position where the first operating light beam is activated, with the movable mirror 8 maintained retracted, the other movable mirror 7 is retracted to allow the second operating light beam to pass along the same optical axis.

The refractive index of the focusing lens for the second operating light beam (having a wavelength of $1.06\mu$) from the YAG laser device is different than for the first operating light beam. Similar to the case of the guide light beam, the focus position correcting lens 4 is provided on the optical path.

The operation of the laser knife device thus constructed will be described with reference to the aforementioned clinal example. The spot of the guide light beam is set at the bone window and the first operating light beam is applied to cut a minute hole in the bone window. Immediately after this, the second operating light beam is emitted. In this case, the second operating light beam effectively reaches the auditory sense cells without being absorbed by the lymph layer in the outer lymph space as a result of which the auditory sense cells are locally coagulated. Most importantly, immediately after the emission of the first operating light beam is suspended, the second operating light beam is emitted along the same optical axis. If the distance between the bone window and the aimed auditory sense cells on the cochlear duct is estimated anatomically in advance, the position of the focus position correcting lens 4 can be adjusted in advance so that a considerably satisfactory result can be obtained because the aimed part of the auditory sense cells is irradiated by the second operating light beam with a high accuracy with the manipulator maintained fixedly held.

Because of the above-described double focus system, the amounts of shift between the position of the focus position correcting lens 4 and the two focal points can be graduated and marked on the lens barrel of the lens 4. The first and second operating light beams can be emitted continuously or intermittently (pulsively). However, this technique is well-known in the art in conventional laser knife devices. In order to apply the second operating light beam immediately after the application of the first operating light beam has been suspended, a technique may be employed in which both of the first and second operating light beams are maintained on, and the application of the second operating light beam is automatically effected in response to the retraction of the movable mirror 7. In this case, while the first operating light beam is applied, the second operating light beam is reflected from the rear surface of the movable mirror 7 to the trap 9, where it is absorbed and radiated as heat. If losses are permitted for the first and second operating light beams, a half-silvered mirror may be employed as the mirror 7 so that the first and second operating light beams can be emitted simultaneously along the same optical axis. This technique provides good security because parts of the first and second operating light beams are then absorbed by the trap 9.

As is apparent from the above description, according to the invention, single and double focus irradiation along with simultaneous and alternate irradiation can be suitably combined in emitting the first and second operating light beams along the same optical axis in accordance with the invention. The various beams are selectively combined by the positioning of the focus position correcting lens 4 and the sequence of operations of the movable mirrors 7 and 8. In the above-described embodiment, the second operating light beam is a YAG laser beam although it may be a visible argon laser beam or an ultraviolet laser beam depending on the intended use. The sequence control of the laser means may be carried out by the double action of a foot pedal or a preprogrammed sequence control may be employed. In the latter case, the foot pedal may be of the single action type. Also, a xenon discharge tube may be used to produce one of the beams.

What is claimed is:

1. A laser knife device comprising first and second operating light beam sources emitting first and second laser light beams of different wave lengths respectively, a guide light source for producing a guide light beam, reflecting means for directing said first and second laser light beams from said first and second operating light beam sources and said guide light beam along a common path, a multi-articulation flexible light conducting device disposed along said common path, a focusing lens provided at an end of said multi-articulation flexible light conducting device, said reflecting means including first moveable mirror means having a first position for reflecting said guide light beam along said common path and a second position for removing said guide light beam from said common path, and second moveable mirror means having a first position for reflecting said first laser light beam along said common path when said first moveable mirror means is in said second position thereof while reflecting said second laser beam elsewhere and a second position permitting passage of said second laser light beam along said common path.

2. The device as claimed in claim 1 further comprising an absorber located in alignment with second moveable mirror means and said first operating light beam source for absorbing said second laser light beam when said second moveable mirror means is in said first position thereof.

3. The device as claimed in claim 1 wherein said first operating light beam source comprises a $CO_2$ laser and wherein said second operating light beam source comprises a YAG laser.

4. The device as claimed in claim 1 wherein said guide light beam source comprises a He—Ne laser.

5. The device as claimed in claim 1 further comprises a first focus position correcting lens positioned in the path of at least one of said laser light beams to focus said laser light beam and a second focus position correcting lens positioned in the path of said guide light beam to focus said guide light beam.

* * * * *